United States Patent [19]

Milner et al.

[11] Patent Number: 5,093,362

[45] Date of Patent: Mar. 3, 1992

[54] INSECTICIDAL COMPOUNDS

[75] Inventors: David J. Milner, Whitefield; Mark A. Spinney, Liphook; Michael J. Robson, Bracknell, all of United Kingdom

[73] Assignee: Imperial Chemical Industries PLC, London, England

[21] Appl. No.: 472,951

[22] Filed: Jan. 31, 1990

[30] Foreign Application Priority Data

Feb. 2, 1989 [GB] United Kingdom ................ 8902324

[51] Int. Cl.$^5$ ............................................. A01N 53/00
[52] U.S. Cl. ........................................ 514/531; 560/124
[58] Field of Search ........................... 560/124; 514/531

[56] References Cited

U.S. PATENT DOCUMENTS

| | | | |
|---|---|---|---|
| 4,024,163 | 5/1977 | Elliott | 560/124 |
| 4,489,093 | 12/1984 | Martel et al. | 424/304 |
| 4,757,127 | 7/1988 | Tessier et al. | 558/141 |
| 4,808,749 | 2/1989 | Martel et al. | 558/434 |
| 4,927,852 | 5/1990 | Robson | 560/124 |
| 4,939,172 | 7/1990 | Cadiergue | 560/124 |

FOREIGN PATENT DOCUMENTS

| | | |
|---|---|---|
| 50534 | 4/1982 | European Pat. Off. . |
| 224417 | 6/1987 | European Pat. Off. . |
| 0281439 | 7/1988 | European Pat. Off. . |

OTHER PUBLICATIONS

Elliott, Chem. Soc. Rev., 7, pp. 473-505 (1978).

*Primary Examiner*—Michael L. Shippen
*Attorney, Agent, or Firm*—Cushman, Darby & Cushman

[57] ABSTRACT

The invention provides compounds of formula:

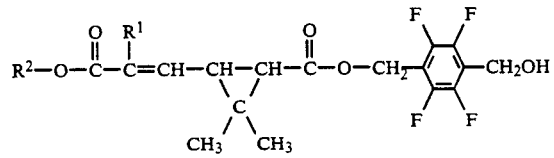

wherein $R^1$ represents hydrogen or halogen and $R^2$ represents $C_{1-8}$ alkyl or $C_{1-8}$ haloalkyl, useful as insecticides and knockdown agents. The invention also provides compositions comprising them, methods of their use in controlling insects, and processes for their preparation.

5 Claims, No Drawings

INSECTICIDAL COMPOUNDS

This invention relates to novel 4-(hydroxymethyl)-2,3,5,6-tetrafluorobenzyl esters useful in combating insects and similar invertebrate pests, to processes for their preparation, to compositions comprising them, and to methods of combating insects and similar invertebrate pests using the compositions.

The esters according to the invention show a high level of contact, residual and fumigate activity. They also exhibit an exceptionally high level of knockdown activity against cockroach species, such as *Blattella germanica*.

In a first aspect, the invention provides a compound having the general formula (I):

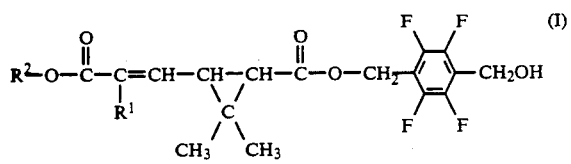

or a stereoisomer thereof, wherein $R^1$ represents hydrogen or halogen and $R^2$ represents $C_{1-8}$ alkyl or $C_{1-8}$ haloalkyl. The term alkyl as used herein refers to both straight and branched chain forms.

The compounds of formula (I) may exist in a number of stereoisomeric forms dependent upon the relative configurations of the substituents at the 1-and 3-positions of the cyclopropane ring and around the carbon-carbon double bond of the 3-ethenyl substituent. The scope of the invention includes all individual isomeric forms and mixtures thereof, including racemates.

Preferred compounds according to the invention are those exhibiting a cis configuration at the cyclopropane ring and those exhibiting an E or predominantly E configuration around the carbon-carbon double bond of the ethenyl substituent when $R^1$ represents halogen, or a Z or predominantly Z configuration when $R^1$ represents hydrogen. Compounds in which $R^1$ represents hydrogen, chlorine or fluorine, and those wherein $R^2$ represents $C_{1-4}$ alkyl or $C_{1-4}$ fluoroalkyl are also preferred.

Examples of compounds according to the invention include the 4-hydroxymethyl-2,3,5,6-tetrafluorobenzyl esters of the following acids, and stereoisomers thereof:

3-(3-methoxy-3-oxoprop-1-en-1-yl)-2,2-dimethylcyclopropanecarboxylic acid;

3-(2-fluoro-3-methoxy-3-oxoprop-1-en-1-yl)-2,2-dimethylcyclopropanecarboxylic acid;

3-(3-ethoxy-3-oxoprop-1-en-1-yl)-2,2 dimethylcyclopropanecarboxylic acid;

3-(2-fluoro-3-ethoxy-3-oxoprop-1-en-1-yl)-2,2-dimethylcyclopropanecarboxylic acid;

3-(3-propoxy-3-oxoprop-1-en-1-yl)-2,2-dimethylcyclopropanecarboxylic acid;

3-(2-fluoro-3-propoxy-3-oxoprop-1-en-1-yl)-2,2-dimethylcyclopropanecarboxylic acid;

3-[3-(1-methylethoxy)-3-oxoprop-1-en-1-yl]-2,2-dimethylcyclopropanecarboxylic acid;

3-[2-fluoro-3-(1-methylethoxy)-3-oxoprop-1-en-1-yl]-2,2-dimethylcyclopropanecarboxylic acid;

3-(3-butoxy-3-oxoprop-1-en-1-yl)-2,2-dimethylcyclopropanecarboxylic acid;

3-(2-fluoro-3-butoxy-3-oxoprop-1-en-1-yl)-2,2-dimethylcyclopropanecarboxylic acid;

3-[3-(1,1-dimethylethoxy)-3-oxoprop-1-en-1-yl]-2,2-dimethylcyclopropanecarboxylic acid;

3-[2-fluoro-3-(1.1-dimethylethoxy)-3-oxoprop-1-en-1-yl]-2,2-dimethylcyclopropanecarboxylic acid;

3-[3-(2,2,2-trifluoroethoxy)-3-oxoprop-1-en-1-yl]-2,2-dimethylcyclopropanecarboxylic acid;

3-[2-fluoro-3-(2,2,2-trifluoroethoxy)-3-oxoprop-1-en-1-yl]-2,2-dimethylcyclopropanecarboxylic acid;

3-[3-(1,1,1,3,3,3-hexafluoroprop-2-yloxy)-3-oxoprop-1-en-1-yl]-2,2-dimethylcyclopropanecarboxylic acid;

3-[2-fluoro-3-(1,1,1,3,3,3-hexafluoroprop-2-yloxy)-3-oxoprop-1-en-1-yl]-2,2-dimethylcyclopropanecarboxylic acid;

3-(2-chloro-3-methoxy-3-oxoprop-1-en-1-yl)-2,2-dimethylcyclopropanecarboxylic acid;

3-(2-chloro-3-ethoxy-3-oxoprop-1-en-1-yl)-2,2-dimethylcyclopropanecarboxylic acid;

3-(2-chloro-3-propoxy-3-oxoprop-1-en-1-yl -2,2-dimethylcyclopropanecarboxylic acid;

3-[2-chloro-3-(1-methylethoxy)-3-oxoprop-1-en-1-yl]-2,2-dimethylcyclopropanecarboxylic acid;

3-(2-chloro-3-butoxy-3-oxoprop-1-en-1-yl -2,2-dimethylcyclopropanecarboxylic acid;

3-[2-chloro-3-(1,1-dimethylethoxy)-3-oxoprop-1-en-1-yl]-2,2-dimethylcyclopropanecarboxylic acid;

3-[2-chloro-3-(2,2,2-trifluoroethoxy)-3-oxoprop-1-en-1-yl]-2,2-dimethylcyclopropanecarboxylic acid; and 3-[2-chloro-3-(1,1,1,3,3,3-hexafluoroprop-2-yloxy)-3-oxoprop-1-en-1-yl]-2,2-dimethylcyclopropanecarboxylic acid.

As particular examples of compounds according to the invention there may be mentioned:

4-hydroxymethyl-2,3,5,6-tetrafluorobenzyl (1RS, cis, E)-3-(2-fluoro-3-methoxy-3-oxoprop-1-en-1-yl)-2,2-dimethylcyclopropanecarboxylate (Compound No. 1);

4-hydroxymethyl-2,3,5,6-tetrafluorobenzyl (1RS, cis, E)-3-(2-chloro-3-propoxy-3-oxoprop-1-en-1-yl)-2,2-dimethylcyclopropanecarboxylate (Compound No, 2);

4-hydroxymethyl-2,3,5,6-tetrafluorobenzyl (1RS, cis, Z)-3-(2-chloro-3-ethoxy-3-oxoprop-1-en-1-yl)-2,2-dimethylcyclopropanecarboxylate (Compound No. 3);

4-hydroxymethyl-2,3,5,6-tetrafluorobenzyl (1RS, cis, Z)-3-(3-methoxy-3-oxoprop-1-en-1-yl)-2,2-dimethylcyclopropanecarboxylate (Compound No. 4):

4-hydroxymethyl-2,3,5,6-tetrafluorobenzyl (1RS, cis, E)-3-(2-chloro-3-methoxy-3-oxoprop-1-en-1-yl)-2,2-dimethylcyclopropanecarboxylate (Compound No. 5);

4-hydroxymethyl-2,3,5,6-tetrafluorobenzyl (1RS, cis, E)-3-(2-fluoro-2-ethoxy-3-oxoprop-1-en-1-yl)-2,2-dimethylcyclopropanecarboxylate (Compound No. 6);

4-hydroxymethyl-2,3,5,6-tetrafluorobenzyl (1RS, cis,Z)-3-(2-ethoxy-3-oxoprop-1-en-1-yl)-2,2-dimethylcyclopropanecarboxylate (Compound No. 7);

4-hydroxymethyl-2,3,5,6-tetrafluorobenzyl (1RS, cis, E)-3-(2-chloro-3-ethoxy-3-oxoprop-1-en-1-yl)-2,2-dimethylcyclopropanecarboxylate (Compound No. 8);

4-hydroxymethyl-2,3,5,6-tetrafluorobenzyl (1RS, cis, E)-3-(2-fluoro-3-propoxy-3-oxoprop-1-en-1-yl)-2,2-dimethylcyclopropanecarboxylate (Compound No. 9); and 4-hydroxymethyl-2,3,5,6-tetrafluorobenzyl (1RS, cis Z)-3-(3-propoxy-3-oxoprop-1-en-1-yl)-2,2-dimethylcyclopropanecarboxylate (Compound No. 10).

The compounds of formula (I) are esters and may be prepared by conventional esterification processes, of which the following are examples:

(a) An acid of formula (II):

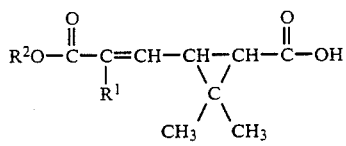

wherein R¹ and R² have any of the meanings given above, may be reacted directly with the alcohol of formula (III):

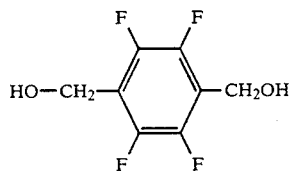

the reaction preferably taking place in the presence of a dehydrating agent, for example a carbodiimide such as dicyclohexylcarbodiimide;

(b) An acid halide of formula (IV):

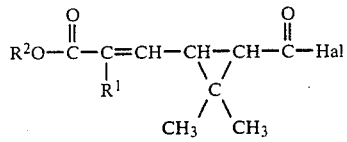

wherein Hal represents a halogen atom, preferably chlorine, and R¹ and R² have any of the meanings given above, may be reacted with the alcohol of formula (III), the reaction preferably taking place in the presence of a base, for example pyridine, a trialkylamine or an alkali metal hydroxide or carbonate;

(c) an acid of formula (II) wherein R¹ and R² have any of the meanings given above, or preferably an alkali metal salt thereof, may be reacted with either (i) a compound of formula (V):

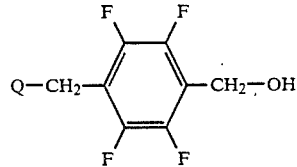

wherein Q represents a halogen atom, preferably bromine or chlorine, or with a quaternary ammonium salt derived from the reaction of such a halide with a tertiary amine, for example pyridine or a trialkylamine such as triethylamine, or (ii) a compound of formula (V) wherein Q represents a displaceable group, for example the mesyloxy or tosyloxy group.

All of these conventional processes for the preparation of esters may be carried out using solvents and diluents for the various reactants where appropriate, and may be accelerated or lead to higher yields of product when performed at elevated temperatures or in the presence of appropriate catalysts, for example phase-transfer catalysts. Those skilled in the art will recognise that the alcohol of formula (III) is a diol and that careful control of the processes (a) and (b) is required to minimize its further reaction at the second hydroxyl function; process (c) has been found to be the most suitable for preparation of the compounds of formula (I).

The preparation of individual isomers may be carried out in the same manner but commencing from the corresponding individual isomers of compounds of formula II or IV. These may be obtained by conventional isomer separation techniques from mixtures of isomers. Thus cis and trans isomers may be separated by, for example, fractional crystallisation of the carboxylic acids or salts thereof, whilst the various optically active species may be obtained by fractional crystallisation of salts of the acids with optically active amines, followed by regeneration of the optically pure acid. The optically pure isomeric form of the acid (or its equivalent acid chloride or ester) may then be reacted with the alcohol of formula (III) or a halide, mesylate or tosylate of formula (V) to produce a compound of formula (I) in the form of an individually pure isomer thereof.

The halides of formula (V) wherein Hal represents chlorine or bromine may be prepared by monohalogenation of the alcohol of formula (III) according to the process described in UK patent application number 2153819A. The alcohol of formula (III) may itself be prepared by the processes described in Scheme I.

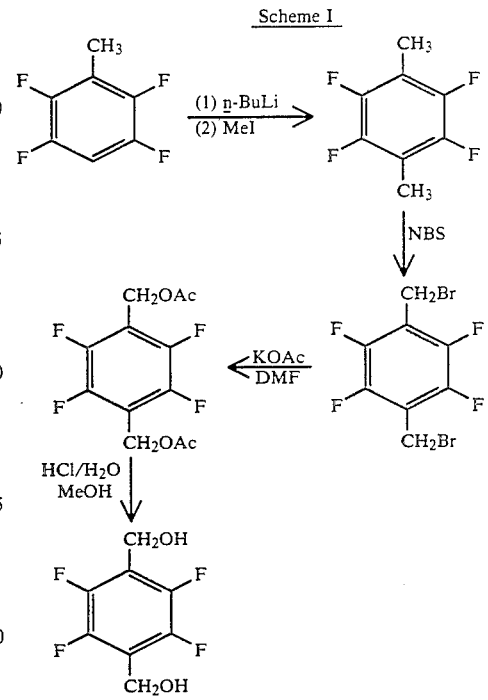

Key:
n-BuLi = n-Butyllithium
NBS = N-bromosuccinimide
DMF = Dimethylformamide
KOAc = Potassium acetate The preparation of acids of formula (II) is described in French Patent Application No. 2,185,612 and in European Patent Application Nos. 38,271, 41,021, 48,186, 50,534 and 94,304. These acids, when produced by Wittig reactions as described in the prior art documents are formed in a mixture of E and Z configurations. They may be used directly in the esterification reaction, or may first be separated into E or Z isomers by standard methods such as chromatography, and in particular by high pressure liquid chromatography.

The preparation of acids of formula (II) wherein $R^1$ represents fluorine and having the cis configuration at the cyclopropane ring may be advantageously achieved by reaction of cis-caronaldehyde with an alkyldiisopropylphosphonofluoroacetate of formula (VI) in the presence of a base, and, optionally, a lithium salt. An example of this reaction is shown in Scheme II.

Scheme II

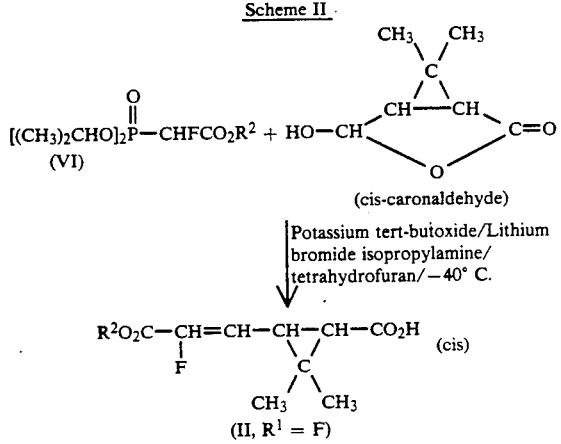

The use of a diisopropylfluorophosphate in the process described in Scheme II has been found, surprisingly, to produce the acids of formula (II) having a high predominance of the E configuration at the ethenyl substituent Cis-Caronaldehyde may be prepared by ozonolysis of cis-chrysanthemic acid by the process described in French Patent No. 1,580,474.

The alkyl diisopropylphosphonofluoroacetates of formula (VI) may be prepared from bromotrifluoroethylene by the process summarised in Scheme III.

Scheme III

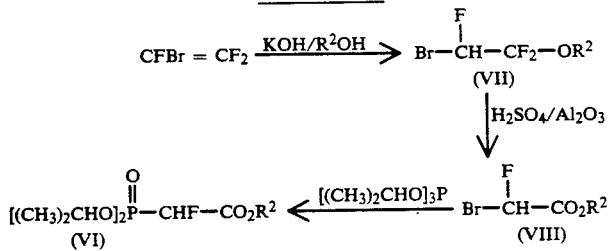

Further details of these processes are given in the Examples.

The compounds of formula (I) may be used to combat and control infestations of insect and acarine pests. The insect and acarine pests which may be combated and controlled by the use of the invention compounds include those pests associated with agriculture (which term includes the rowing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula (I) suitable inert diluent or carrier materials, and/or surface active agents.

The compounds of the invention may be the sole active ingredient of the composition or they may be admixed with one or more additional active ingredients such as insecticides, insecticide synergist, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compounds of the invention or complement the activity for example by increasing the speed of effect, improving kill or knockdown of target insect pests, or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:

(a) Pyrethroids such as permethrin, esfenvalerate, deltamethrin, cyhalothrin, biphenthrin, fenpropathrin, cyfluthrin, tefluthrin, empenthrin, fish safe pyrethroids for example ethofenprox, natural pyrethrins, tetramethrin, s-bioallethrin, fenfluthrin, prallethrin, 5-benzyl-3-furylmethyl-(E)-(1R,3S)-2,2-dimethyl-3-(2-oxothiolan-3-ylidenemethyl)cyclopropane carboxylate, and pentafluorobenzyl (cis)-3-[2-fluoro-2-(methoxycarbonyl)ethenyl]-2,2-dimethylcyclopropane-carboxylate.

(b) Organophosphates such as profenofos, sulprofos, dichlorvos, methyl parathion, azinphos-methyl, demeton-s-methyl, heptenophos, thiometon, fenamiphos, monocrotophos, profenophos, triazophos, methamidophos, dimethoate, phosphamidon, malathion, chlorpyrifos, phosalone, fensulfothion, fonofos, phorate, phoxim, pyrimiphos-methyl, fenitrothion and diazinon;

(c) Carbamates (including aryl carbamates) such as pirimicarb, cloethocarb, carbofuran, ethiofencarb, aldicarb, thiofurox, carbosulfan, bendiocarb, fenobucarb, propoxur and oxamyl;

(d) Benzoyl ureas such as triflumuron, chlorofluazuron;
(e) Organic tin compounds such as cyhexatin, fenbutatin oxide, azocyclotin;
(f) Macrolides such as avermectins or milbemycins, for example such as abamectin, avermectin, and milbemycin;
(g) Hormones and synthetic mimics thereof such as juvenile hormone, juvabione, ecdysones, methoprene and hydroprene.
(h) Pheromones.
(i) Organochlorine compounds such as benzene hexachloride, DDT, chlordane or dieldrin.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin, can be employed. Alternatively insecticides or acaricides specific for particular insect species/stages for example ovolarvicides such as clofentezine, amitraz, chlordimeform, flubenzimine, hexythiazox and tetradifon, motilicides such as dicofol or propargite, adulticides such as bromopropylate, chlorobenzilate, or insect growth regulators such as hydramethylnon, cyromazine, methoprene, chlorfluazuron and diflubenzuron may also be included in the compositions.

Examples of suitable insecticide synergists for use in the compositions include piperonyl butoxide, sesamex, and dodecyl imidazole.

Suitable herbicides, fungicides and plant growth regulators for inclusion in the compositions will depend upon the intended target and the effect required. An example of a rice selective herbicide which can be included is propanil, an example of a plant growth regulator for use in cotton is "Pix", and examples of fungicides for use in rice include blasticides such as blasticidin-S. The choice of other ingredients to be used in mixture with the active ingredient will often be within the normal skill of the formulator, and will be made from known alternatives depending upon the total effect to be achieved.

The ratio of the compound of the invention to any other active ingredient in the composition will depend upon a number of factors including the type of insect pests to be controlled, and the effects required from the mixture. However in general, the additional active ingredient of the composition will be applied at about the rate it would usually be employed if used on its own, or at a lower rate if synergism occurs.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous qranular material, for example pumice.

Alternatively the compositions may be in the form of liquid preparations to be used as dips, sprays or aerosols. Dips and sprays are generally aqueous dispersions or emulsions of the active ingredient in the presence of one or more known wetting agents, dispersing agents or emulsifying agents (surface active agents). Aerosol compositions may contain the active ingredient or ingredients, a propellant and an inert diluent, for example odourless kerosene or alkylated benzenes. In a preferred form, aerosol compositions may contain from 0.005% to 4% of active ingredient or ingredients, the remainder of the composition comprising a solvent, selected from odourless kerosine and alkylated benzenes, and a propellant. Aerosol compositions may optionally incorporate other additives, for example perfumes or corrosion inhibitors.

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and optionally adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonqed periods and after such storage, to be capable of dilution with water to form aqueous preparations which remain homogenous for a sufficient time to enable them to be applied by conventional spray equipment. The concentrates may contain 1-99% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compounds of formula (I) and compositions comprising them are very toxic to wide varieties of insect, acarine and other invertebrate pests, including, for example, the following :

*Myzus persicae* (aphids)

*Aphis gossvpii* (aphids)
*Aphis fabae* (aphids)
*Megoura viceae* (aphids)
*Aedes aecypti* (mosquitos)
Anopheles spp. (mosquitos)
Culex spp. (mosquitos)
*Dysdercus fasciatus* (capsids)
*Musca domestica* (houseflies)
*Pieris brassicae* (white butterfly, larvae)
*Plutella maculipennis* (diamond back moth, larvae)
*Phaedon cochleariae* (mustard beetle)
Aonidiella spp. (scale insects)
Trialeuroides spp. (white flies)
*Bemisia tabaci* (white flies)
*Blattella germanica* (cockroaches)
*Periplaneta americana* (cockroaches)
*Blatta orientalis* (cockroaches)
*Spodoptera littoralis* (cotton leaf worm)
*Heliothis virescens* (tobacco budworms)
*Chortiocetes terminifera* (locusts)
Diabrotica spp. (rootworms)
Agrotis spp. (cutworms)
*Chilo partellus* (maize stem borers)
*Nilaoarvata lucens* (plant hoppers)
*Nephotettix cincticeps* (leaf hoppers)
*Panonvchus ulmi* (European red mite)
*Panonvchus citri* (citrus red mite)
*Tetranychus urticae* (two-spotted spider mite)
*Tetranychus cinnabarinus* (carmine spider mite)
*Phyllocoptruta oleivora* (citrus rust mite)
Polyphacotarsonemus latus (broad mite)
Brevioalpus spp. (mites).

The compounds according to formula (I) and compositions comprising them have been shown to be particularly useful in controlling lepidopteran pests of cotton, for example Spodoptera spp. and Heliothis spp. They have also been shown to be particularly useful in combating pests which inhabit the soil, for example Diabrotica spp. They also exhibit exceptionally high levels of knockdown activity against cockroach species such as *Blattella germanica*. The compounds of formula (I) also show knockdown activity against other public health pests, for example *Musca domestcia*. The knockdown activity may be further improved by application of the compounds in combination with a penetrant, for example N-vinylpyrollidine, n-octylbenzene or dodecylimidazole. They may also be useful in combating insect and acarine pests which infest domestic animals, such as *Lucilia sericata* and ixodid tickssuch as Boophilus spp., Ixodes spp., Amblyomma spp., Rhipicephalus spp., and Dermocentor spp. They are effective in combating both susceptible and resistant strains of these pests in their adult, larval and intermediate stages of growth, and may be applied to the infested host animal by topical, oral or parental administration.

The following Examples illustrates various aspects of this invention. In the preparation Examples the products were usually identified and characterised by means of nuclear magnetic reasonance (NMR) spectroscopy and infra red (IR) spectroscopy. In each case where a product is specifically named its spectral characteristics are consistent with the assigned structure. Except where stated otherwise, exemplified compounds having one or more asymmetrically substituted carbon atoms were prepared in racemic form.

In the Examples, Gas Liquid Chromatography GLC) retention times were determined on a Hewlett Packard 5890 Gas Chromatography, using a Chrompak, CPSil 5CB column of 12.5M length and 0.2 mm internal diameter. Unless otherwise stated, the injection temperature was 100° C., and a temperature gradient of 15° C./minute employed, upto a maximum temperature of 280° C., maintained for 4 minutes. The carrier gas was helium at a column head pressure maintained at 11 psi.

Alternative injection and maximum temperatures are indicated in the Examples where appropriate.

$^1$H Nuclear Magnetic Resonance (NMR) spectometry was performed at a frequency of 270 MHz on a Jeol FX 270 NMR spectrometer, unless otherwise indicated. 90 MHz, 60 MHz, 250 MHz and 400 MHz $^1$H NMR spectrometry were performed using Jeol FX 90Q, Brucker WH90, Jeol PMX 60S, Brucker WM250, and Jeol GX400 spectrometers.

$^{19}$F NMR spectrometry was performed on a Jeol FX90Q spectrometer at a frequency of 84.26 MHz. All NMR shift ($\delta$) values are quoted in ppm relative to a standard (TMS or CFCl$_3$) In the NMR data, the following abbreviations are used :
s = singlet
d = doublet
t = triplet
q = quartet
dd = double doublet
m = multiplet
b = broad Molecular Ion (M+) peaks were determined on one of three mass spectrometers : Jeol DX303, Kratos MS80 or Hewlett Packard HP 5992.

EXAMPLE 1

This Example illustrates the stages in the preparation of (IRS, cis, E)-3-(3-methoxy-3-oxoprop-1-en-1-yl)-2,2-dimethylcyclopropanecarboxylic acid.

Stage 1: 1-Bromo-1,2,2-trifluoro-2-methoxyethane.

An autoclave of 250 cm$^3$ capacity was charged with a solution of potassium hydroxide (0.2 mol, 11 g) in methanol (2 mol, 64 g). The autoclave was sealed and connected by metal piping to a weighed cylinder of bromotrifluoroethylene. The olefin was introduced in portions and the cylinder weighed after each introduction. On introduction of the first batch of bromotrifluoroethylene (30 g), a rapid rise in the temperature of the mixture was observed to 72° C. within a minute. The stirred mixture was allowed to cool to 30° C. and a further batch of olefin (10 g) added (mild exotherm to 33° C.). The mixture was stirred for a further 1 hour, and then the autoclave opened. The products were drowned into water (500 cm$^3$) and the lower organic layer (27.8 g) which separated was collected and identified as 1-bromo-1,2,2-trifluoro-2-methoxyethane, yield 77%.

$^1$H NMR (CDCl$_3$): 6.5 (t,0.5H); 6.0 (t,0.5H); 3.7 (s,3H).

Stage 2: Methyl bromofluoroacetate

A mixture of 1-bromo-1,2,2-trifluoro-2-methoxyethane (20 g, 0.1 mol) and concentrated sulphuric acid (0.1 g) was heated at the reflux temperature in the presence of fused alumina antibumping granules (5 g) over a period of 1 hour (temperature gradually raised from 88° C. to 106° C.). The mixture was allowed to cool to the ambient temperature and the crude hydrolysis product was decanted from the solid granules. Yield 16.9 g (96%). The crude ester was purified by distillation at atmosphere pressure (boiling point 135° C.).

$^1$H NMR (CDCl$_3$): 7.0 (s,0.5H); 6.2 (s,0.5H); 3.9 (s,3H).

Stage 3: Methyl diisopropylphosphonofluoroacetate (i) Triisopropyl phosphite

To isopropanol (186 g, 3.1 mol), pyridine (3.0 mol, 237 g) and ether (1000 cm$^3$), cooled to 10° C., there was added, with stirring over 1 hour, phosphorus trichloride (87cm$^3$, 1.0 mol) over 30 minutes so that the reaction temperature did not reach 15° C. The mixture was filtered, the solids washed with ether and the solvent removed by evaporation under reduced pressure to leave a viscous yellow oil (167 g) which was purified by distillation under reduced pressure. This product was identified as triisopropyl phosphite.

Boiling point: 70°–78° C. (20 mm Hg), $^1$HNMR (CDCl$_3$): 1.2 (d,18H); 4.3 (m, 3H).

(ii) Methyl diisopropylphosphonofluoroacetate

Methyl bromofluoroacetate (17.1q) was mixed with triisopropyl phosphite (41.6 g) and heated with stirring at intervals and analysed by GLC. After 5.5 hours, all of the initial ester had been consumed. The mixture was cooled to the ambient temperature, and excess triisopropyl phosphite was removed by distillation at reduced pressure (52° C./1.5 mm Hg). The straw-coloured residue (19.7 g was identified as substantially pure methyl diisopropylphosphonofluoroacetate.

$^1$H NMR (CDCl$_3$): 1.3 (d, 12H); 3.8 (s,3H); 4.5–5.5 (m,3H).

Stage 4: (1RS cis, E)-3-(3-methoxy-3-oxoprop-1-en-1-yl)-2,2-dimethylcyclopropanecarboxylic acid Diisopropylamine (dried) (7.9cm$^3$, 0.056 mol), cis-caronaldehyde (9.85 g, 0.069 mol), prepared by ozonolysis of cis-chrysanthemic acid, as described in French Patent No 1,580,474, and methyl diisopropylphosphonofluoroacetate (19.7 g 0.077 mol) were added successively at 40° C. to a stirred solution of dried lithium bromide (19.7 g, 0.226 mol) in dried tetrahydrofuran (390cm$^3$). A suspension of potassium t-butoxide (19.7 g, 0.176 mol) in dried tetrahydrofuran (400 cm$^3$) was then added to the stirred mixture over 15 minutes at 40° C. The yellow mixture was poured into 2 molar aqueous hydrochloric acid solution (1000 cm$^3$) and the product extracted into diethyl ether (2×300 cm$^3$). The organic layers were combined, dried over anhydrous magnesium sulphate, filtered and evaporated under reduced pressure to give a crude product (25.3 g) which was dissolved in dichloromethane (200 cm$^3$) and back-extracted into aqueous sodium bicarbonate solution (2×300 cm$^3$). The aqueous phase was acidified to pH 1.0 with 2 molar aqueous hydrochloric acid solution and the product extracted into diethyl ether (2×300 cm$^3$). Evaporation of the solvent under reduced pressure gave 14 g of a viscous oil which crystallised on standing. The product was recrystallised from hexane to give (1RS cis, E)-3-(2-fluoro-3-methoxy-3-oxoprop-1-en-1-yl)-2,2-dimethylcyclopropanecarboxylic acid (7.9 g) as a colourless crystalline solid.

Melting point: 89° C.

$^1$NMR (CDCl$_3$): 1.3 (s,6H); 1.93 (d,1H); 2.9 (t,1H); 3.85(s,3H); 6.4 (q,1H); plus (s,1H) found in a 20 ppm downfield scan, attributed to CO$_2$H.

EXAMPLE 2

This Example illustrates the preparation of 4-hydroxymethyl-2,3,5,6-tetrafluorobenzyl (1RS cis, E)-3-(2-fluoro-3-methoxy-3-oxoprop-1-en-1-yl)-2,2-dimethylcyclopropanecarboxylate (Compound No 1).

A mixture of (1RS cis,E)-3-(2-fluoro-3-methoxy-3-oxoprop-1-en-1-yl)-2,2-dimethylcyclopropanecarboxylic acid (0.5 g), 4-bromomethyl-2,3,5,6-tetrafluorobenzyl alcohol (0.59 g, prepared according to the method described in UK Patent Application No 2153819A), anhydrous potassium carbonate (0.34 g) and methyl ethyl ketone (25 cm$^3$) was heated at the reflux temperature for 5 hours. The mixture was allowed to cool to the ambient temperature and was then stood for 17 hours. After filtration, the filtrate was evaporated under reduced pressure to leave a pale brown oil (0.8 g). The crude product was purified by preparative thin layer chromatography on a silica gel support, eluting with hexane containing 50% by volume diethyl ether. The product was recovered from the silica support by dissolution in ethyl acetate and evaporation of the solvent under reduced pressure, and obtained as a pale orange oil (0.45 g), identified as the title product.

$^1$H NMR (CDCl$_3$): 1.3 (s,6H); 1.9 (d,1H); 2.9 (t,1H); 3.85 (s,3H); 4.8 (s,2H); 5.2 (s,2H); 6.4 (s,1H).

EXAMPLE 3

This Example illustrates the stages in the preparation of (1RS, cis, E/Z)-3-(2-chloro-3-propoxy-3-oxoprop-1-en-1-yl)-2,2-dimethyl-cyclopropanecarboxylic acid, and the separation of the E and Z isomers Stage 1: Propyl diethylphosphonoacetate Titanium IV propoxide (12.1 g) was added to a stirred mixture of ethyl diethylphosphonoacetate (100.4 g) and n-propanol (610 cm$^3$) under a nitrogen atmosphere. The mixture was stirred at the ambient temperature for a total of 18 hours, after which time analysis of the mixture showed that the reaction was complete. The volatile components were removed by distillation firstly at atmospheric pressure and then under reduced pressure on a rotary evaporator. 1.5 M aqueous hydrochloric acid (350cm$^3$) was added to the crude product and the mixture extracted with diethyl ether. The organic layer was separated and washed with further 1.5 M aqueous hydrochloric acid solution. The aqueous phases were combined and extracted with more diethyl ether (2×100cm$^3$). All of the organic layers were combined, washed with water and dried over anhydrous magnesium sulphate. Evaporation of the solvent under reduced pressure gave a yellow oil (85.4 g) which was used without further purification.

GLC Retention time: 3.19 minutes,

Stage 2: Propyl diethylphosphonodichloroacetate.

A cooled (0° C.) mixture of chloros (aqueous sodium hypochlorite solution, 610cm$^3$) and water (300cm$^3$) was adjusted to pH6 by the addition of concentrated aqueous hydrochloric acid solution. Propyl diethylphosphonoacetate (82.2 g) was added simultaneously with the acid. A vigorous exotherm was noted (the temperature rose to 16° C.). Stirring was continued at 12° C. for 6 minutes and dichloromethane (500cm$^3$) was added. After 3 minutes of stirring, the dichloromethane layer was separated. The aqueous phase was washed with further dichloromethane (3×200cm$^3$). The combined organic layers were dried over anhydrous magnesium sulphate and the solvent evaporated under reduced pressure to leave the title compound as a yellow oil (111 g) which was stored under high vacuum to remove volatile components (final yield 101.1 g. The product was used without further purification.

GLC Retention Time: 7.95 minutes,

Molecular Ion: 264,

Stage 3: Propyl diethylphosphonochloroacetate.

A solution of sodium sulphite (78.6 g) in water (2000 cm$^3$) was added dropwise to a cooled solution of propyl diethylphosphonodichloroacetate (95.7 g) in ethanol (408cm$^3$) over a period of 70 minutes, the temperature of the mixture being maintained below 8° C. during the addition by external cooling. The mixture was stirred at 8° C. for 10 minutes, then without external cooling for a further 15 minutes. Chloroform (100cm$^3$) was added and the mixture stirred vigourously for 3 minutes. The chloroform phase was separated and combined with further chloroform extracts of the aqueous phase, The combined organic layers were dried over anhydrous magnesium sulphate and the solvent evaporated under reduced pressure to give the crude product as a yellow oil from which volatile compounds were removed by storage under high vacuum. The crude product was purified by distillation under reduced pressure to give a colourless liquid (75.2 g)

Boiling Pt. 117°–118° C. (0.61 kPa)

$^1$H NMR (CDCl$_3$): 4.55 (1H, d); 4.20 (6H, m); 1.75 (2H, sextet); 1.4 (6H, t); 1.0 (3H, t).

Stage 4: (1RS, cis,E/Z)-3-(2-chloro-3-propoxy-3-oxo-prop-1-en-1-yl)-2,2-dimethylcyclopropanecarboxylic acid.

Prepared from propyl diethylphosphonochloroacetate and cis-caronaldehyde by the method of Example 1, Stage 4. However, reaction was shown to be incomplete after 2 hours at −40° C. The mixture was allowed to warm gradually to 0° C. (by stages), and finally to 10° C. at which point analysis of a withdrawn sample by gas liquid chromatography showed only traces of starting materials $^1$H NMR (CDCl$_3$): 1.0 (3H,t); 1.3 (6H, t); 1.75 (2H, m); 1.95, 2.05 ($^1$H, 2xd, split due to E and Z isomers); 3.0, 2.35 (1H, 2xt , split due to E and Z isomers); 4.2 (2H, m); 7.45, 6.85 (1H, 2xd, split due to E and Z isomers).

E/Z ratio approximately 1: 0.75 based on NMR analysis.

Stage 5: Isomer separation.

The product of Stage 4 was separated into E and Z isomers by preparative scale high pressure liquid chromatography on a silica column (230–400 mesh) of 30 cm length and 4.5 cm width. The eluent was a mixture of hexane (74.8%), diethyl ether (25%) and acetic acid (0.2%) at a flow rate of 90cm$^3$/min.

Two fractions were collected:

Fraction A: (1RS, cis, E)-3-(2-chloro-3-propoxy-3-oxoprop-1-en-1-yl)-2,2-dimethylcyclopropanecarboxylic acid, retention time 6.8 minutes $^1$H NMR (CDCl$_3$) 1.0 (3H,t); 1.30 (6H,d); 1.75 (2H, sextet); 1.95 (1H, d); 3.0 (1H,t); 4.2 (2H, t); 6.85 (1H, d).

Fraction B: (1RS, cis, Z)-3-(2-chloro-3-propoxy-3-oxoprop-1-en-1-yl)-2,2-dimethylcyclopropanecarboxylic acid), retention time 12.5 mins.

$^1$H NMR (CDCl$_3$): 1.0 (3H, t); 1.70 (2H, s); 2.05 (1H, d); 2.35 (1H, t); 4.2 (2H, t); 7.45 (1H, d).

EXAMPLE 4

4-hydroxymethyl-2,3,5,6-tetrafluorobenzyl (1RS, cis, E)-3-(2-chloro-3-propoxy-3-oxoprop-1-en-1-yl)-2,2-dimethylcyclopropanecarboxylate (Compound No. 2) was prepared according to the method of Example 2.

$^1$H NMR (CDCl$_3$): 1.0 (3H,t); 1.30 (6H, d); 1.75 (2H, sextet); 1.95 (1H, d); 2.95 (1H, dd); 4.20 (2H, t); 4.85 (2H, s); 5.20 (2H,q); 6.85 (1H, d).

EXAMPLE 5

(1RS, cis, E/Z)-3-(3-ethoxy-2-chloro-3-oxoprop-1-en-1-yl)-2,2-dimethylcyclopropanecarboxylic acid was prepared from ethyl diethylphosphonoacetate by processes analogous to those described in Stages 2–4 of Example 3. The E and Z isomers were separated by preparative scale high pressure liquid chromatography under conditions similar to those described in Example 3, stage 5.

Fraction A: (1RS, cis, E)-3-(3-ethoxy-2-chloro-3-oxoprop-1-en-1-yl)-2,2-dimethylcyclopropanecarboxylic acid. Retention time 7.1 minutes.

$^1$H NMR (CDCl$_3$): 1.3 (9H,q); 1.95 (1H, d); 3.00 (1H, t); 4.30 (2H, q); 6.85 (1H,d).

Fraction B: (1RS, cis, Z)-3-(3-ethoxy-2-chloro-3-oxoprop-1-en-1-yl)-2,2-dimethylcyclopropanecarboxylic acid. Retention time 14.0 minutes.

$^1$H NMR (CDCl$_3$): 1.3 (9H, q); 2.05 (1H, d); 2.35 (1H, t); 4.30 (2H, q); 7.40 (1H,d).

EXAMPLE 6

4-hydroxymethyl-2,3,5,6-tetrafluorobenzyl (1RS, cis,Z)-3-(3-ethoxy-2-chloro-3-oxoprop-1-en-1-yl)-2,2-dimethylcyclopropanecarboxylate (Compound No. 3) was prepared according to the method of Example 2.

$^1$H NMR (CDCl$_3$): 1.3 (9H, d+t); 2.0 (1H, d); 2.10 (1H, bt); 2.3 (1H, dd); 4.3 (2H, q); 4.8 (2H, d); 5.2 (2H, d); 7.4 (1H, d).

Further coupling visible.

EXAMPLE 7

This Example illustrates the insecticidal properties of the Products of this invention.

The activity of the Product was determined using a variety of insect pests. The Product was used in the form of liquid preparations containing 500, 250 or 100 parts per million (ppm) by weight of the Product. The preparations were made by dissolving the Product in acetone and diluting the solutions with water containing 0.01% by weight of a wetting agent sold under the trade name "SYNPERONIC" NX until the liquid preparations contained the required concentration of the Product. "SYNPERONIC" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to three days after the treatment.

The results of the tests are given in Table II for each of the Products, at the rate in parts per million given in the second column as a grading of mortality designated as A, B or C wherein A indicates 80–100% mortality, B indicates 50–79% mortality and C indicates less than 50% mortality.

In Table II the pest organism used is designated by a letter code and the pests species, the support medium or food, and the type and duration of test is given in Table I.

TABLE I

| CODE LETTERS (Table II) | TEST SPECIES | SUPPORT MEDIUM/FOOD | TYPE OF TEST | DURATION (days) |
|---|---|---|---|---|
| TUa | *Tetranychus urticae* | French bean | Contact | 3 |

TABLE I-continued

| CODE LETTERS (Table II) | TEST SPECIES | SUPPORT MEDIUM/FOOD | TYPE OF TEST | DURATION (days) |
|---|---|---|---|---|
| | (spider) mites - adult) | leaf | | |
| MP | *Myzus persicae* (aphids) | Chinese Cabbage leaf | Contact | 3 |
| NC | *Nephotettix virescers* (green leaf hopper - nymphs) | Rice plant | Contact | 2 |
| HV | *Heliothis virescens* (tobacco budworm - larvae) | Cotton leaf | Residual | 2 |
| DB | *Diabrotica balteata* (rootworm larvae) | Filter paper/ maize seed | Residual | 2 |
| BG | *Blattella germanica* (cockroach nymphs) | Plastic pot | Residual | 3 |
| MD | *Musca domestica* (houseflies - adults) | Cotton wool/ sugar | Contact | 3 |
| SP | *Spodoptera exigua* (lesser army worm - larvae) | Cotton leaf | Residual | 2 |

"Contact" test indicates that both pests and medium were treated and "residual" indicates that the medium was treated before infestation with the pests.

TABLE II

| Compound No | Example No | Rate (ppm) | TUa | MP | NC | HV | DB | BG | MD | SP |
|---|---|---|---|---|---|---|---|---|---|---|
| 1 | 2 | 100 | C | A | B | C | B | B | C | B |

EXAMPLE 8

This Example illustrates the knockdown activity of the compounds according to the invention.

*Blattella germanica* knockdown test :

The test compound was dissolved in acetone (2 cm³) and the solution diluted to the required concentration with kerosene. 1 cm³ of this preparation was sprayed directly onto 10 *Blattella cermanica* (adult males) held in a netted plastic pot in a Burkhard Potter Tower. Assessment of knockdown was performed at intervals of 15 seconds until all insects were knocked down. On removal from the Burkhard Potter Tower, the insects were held at 25° C. and 65% relative humidity for 48 hours, and an assessment of mortality performed. Each test was replicated three times. The knockdown assessments were analysed to give $KT_{50}$ and $KT_{90}$ values (the time taken, in minutes, to knock down 50% and 90% of the test insects). These values are recorded in Tables III and IV for the test compounds and also for standard tests performed for comparison purposes using Natural Pyrethrins as the active material.

TABLE III

| TEST COMPOUND | RATE (ppm) | $KT_{50}$ (mins) | $KT_{90}$ (mins) |
|---|---|---|---|
| Compound No 1 | 2500 | 0.05 | 0.1 |
| Compound No 1 | 625 | 0.145 | 0.315 |
| Compound No 1 | 156.25 | 0.297 | 0.539 |
| Natural Pyrethrins | 2500 | 0.21 | 0.52 |
| Natural Pyrethrins | 625 | 0.56 | 1.4 |
| Natural Pyrethrins | 156.25 | 1.69 | 2.65 |

TABLE IV

| TEST COMPOUND | RATE (ppm) | $KT_{50}$ (mins) | $KT_{90}$ (mins) |
|---|---|---|---|
| Compound No 2 | 2500 | 0.17 | 0.35 |
| Compound No 2 | 625 | 0.38 | 0.69 |
| Compound No 2 | 156.25 | 0.79 | 1.25 |
| Compound No 3 | 2500 | 0.195 | 0.41 |
| Compound No 3 | 625 | 0.75 | 1.13 |
| Compound No 3 | 156.25 | 2.14 | 3.38 |
| Natural Pyrethrins | 2500 | 0.27 | 0.53 |
| Natural Pyrethrins | 625 | 1.11 | 1.58 |
| Natural Pyrethrins | 156.25 | 3.16 | 6.17 |

EXAMPLE 9

This Example illustrates the composition of typical preparations, or concentrates thereof, which may be used for the application of the compounds according to the invention when used for the control of insect pests. The high level of knockdown activity of the compounds of the invention renders them particularly suitable for admixture with known killing agents for the purposes of providing a preparation which causes rapid knockdown followed by kill of the target pest. As the compounds according to the invention themselves exhibit a lethal effect, admixture with other killing agents is optional.

Examples of killing agents which may be used in the following examples include, but are not limited to, permethrin, cypermethrin, cyhalothrin, lambda-cyhalothrin and pirimiphos-methyl.

| | % Weight |
|---|---|
| (i) Aerosol concentrate: | |
| Compound No. 1 | 10 |
| Optional killing agent | 30 |
| Alkylated benzene solvent (e.g. SOLVESSO 100) | to 100% |
| (ii) Aerosol: | |
| Aerosol concentrate (as in (i) above | 1 |
| Odourless kerosene | 25 |
| Liquid propane gas propellant (e.g. CALOR 48) | 62 |
| Methylene dichloride | 12 |
| (iii) Ready for use formulation: | |
| Aerosol concentrate (as in (i) above | 1 |
| Odourless kerosene | 99 |
| (iv) Hot/cold fogging concentrate: | |
| Compound No 1 | 10 |
| Optional killing agent | 25 |

| | % Weight |
|---|---|
| Alkylated benzene solvent (e.g. SOLVESSO 200) | 50 |
| Paraffinic solvent (e.g. EXSOL D200/240) | to 100% |
| (v) Oil/water dilutable ultra low volume (ULV) formulation: | |
| Compound No 1 | 3 |
| Optional killing agent | 10 |
| Calcium dodecylbenzenesulphonate (e.g. CALX) | 3 |
| Nonylphenol ethoxylate/propoxylate (e.g. SYNPERONIC NPE1800) | 4.5 |
| Alkylated benzene solvent (e.g. SOLVESSO 200) | 40 |
| Paraffinic solvent (e.g. EXSOL D200/240) | to 100% |
| (vi) Oil dilutable ultra low volume (ULV) formulation: | |
| Compound No 1 | 3 |
| Optional killing agent | 10 |
| Alkylated benzene solvent (e.g. SOLVESSO 200) | 50 |
| Paraffinic solvent (e.g. EXSOL D200/400) | to 100% |

Note:
SOLVESSO, CALOR, EXSOL, CALX and SYNPERONIC are registered trade marks.

We claim:

1. A compound having the general formula (I):

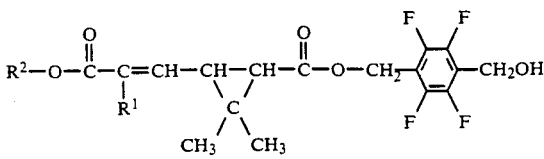

exhibiting the E configuration, wherein $R^1$ represents fluorine and $R^2$ represents $C_{1-4}$ alkyl or $C_{1-4}$ haloalkyl.

2. A compound as claimed in claim 1 exhibiting a cis configuration at the cyclopropane ring.

3. The 4-hydroxymethyl-2,3,5,6-tetrafluorobenzyl ester of an acid selected from the group of acids consisting of:

3-(2-fluoro-3-methoxy-3-oxoprop-1-en-1-yl)-2,2-dimethylcyclopropanecarboxylic acid;

3-(2-fluoro-3-ethoxy-3-oxoprop-1-en-1-yl)-2,2-dimethylcyclopropanecarboxylic acid;

3-(2-fluoro-3-propoxy-3-oxoprop-1-en-yl)-2,2-dimethylcyclopropanecarboxylic acid;

3-[2-fluoro-3-(1-methylethoxy)-3-oxoprop-1-en-1-yl]-2,2-dimethylcyclopropanecarboxylic acid;

3-(2-fluoro-3-butoxy-3-oxoprop-1-en-1-yl)-2,2-dimethylcyclopropanecarboxylic acid;

3-[2-fluoro-3-(1,1-dimethylethoxy)-3-oxoprop-1-en-1-yl]-2,2-dimethylcyclopropanecarboxylic acid;

3-[2-fluoro-3-(2,2,2-trifluoroethoxy)-3-oxoprop-1-en-1-yl]-2,2-dimethylcyclopropanecarboxylic acid;

3-[2-fluoro-3-(1,1,1,3,3,3-hexafluoroprop-2-yloxy)-3-oxoprop-1-en-1-yl]-2,2-dimethylcyclopropanecarboxylic acid.

4. A composition for controlling cockroach pests comprising an effective amount of compound according to claim 1 in association with an insecticidally insert diluent or carrier.

5. A method of combating cockroach pests at a locus which comprises applying to the locus an effective amount of a composition according to claim 4.

* * * * *